United States Patent [19]
Slamin

[11] Patent Number: 5,879,391
[45] Date of Patent: Mar. 9, 1999

[54] MODULAR PROSTHESIS

[75] Inventor: John E. Slamin, Wrentham, Mass.

[73] Assignee: Johnson & Johnson Professional, Inc., Raynham, Mass.

[21] Appl. No.: 720,557

[22] Filed: Sep. 30, 1996

[51] Int. Cl.⁶ .................................................. A61F 2/38
[52] U.S. Cl. .............................................................. 623/20
[58] Field of Search ................................ 623/16, 18, 20, 623/23; 606/69, 70, 71, 72, 73

[56] References Cited

U.S. PATENT DOCUMENTS

| | | | |
|---|---|---|---|
| Re. 28,841 | 6/1976 | Akkgower et al. ...................... | 606/69 |
| 3,534,731 | 10/1970 | Muller ...................................... | 606/69 |
| 4,213,209 | 7/1980 | Install et al. ............................. | 3/1.911 |
| 4,219,893 | 9/1980 | Noiles . | |
| 4,301,553 | 11/1981 | Noiles . | |
| 4,309,778 | 1/1982 | Buechel et al. .......................... | 3/1.911 |
| 4,495,664 | 1/1985 | Blanquaert . | |
| 4,624,673 | 11/1986 | Meyer ....................................... | 623/16 |
| 4,696,290 | 9/1987 | Steffee ..................................... | 606/69 |
| 4,713,076 | 12/1987 | Draenert ................................... | 623/16 |
| 4,790,852 | 12/1988 | Noiles ...................................... | 623/18 |
| 4,822,366 | 4/1989 | Bolesky ................................... | 623/20 |
| 4,846,839 | 7/1989 | Noiles ...................................... | 623/18 |
| 4,888,021 | 12/1989 | Forte et al. ............................... | 623/20 |
| 4,904,110 | 2/1990 | Klein ........................................ | 403/379 |
| 4,950,297 | 8/1990 | Elloy et al. ............................... | 623/20 |
| 4,959,071 | 9/1990 | Brown et al. ............................. | 623/20 |
| 4,985,037 | 1/1991 | Petersen ................................... | 628/20 |
| 5,007,931 | 4/1991 | Smith ....................................... | 623/23 |
| 5,011,496 | 4/1991 | Forte et al. ............................... | 623/20 |
| 5,019,103 | 5/1991 | Van Zile et al. ......................... | 623/20 |
| 5,061,286 | 10/1991 | Lyle ......................................... | 623/16 |
| 5,127,914 | 7/1992 | Calderale et al. ........................ | 606/65 |
| 5,133,760 | 7/1992 | Petersen et al. .......................... | 623/20 |
| 5,152,796 | 10/1992 | Slamin ..................................... | 623/20 |
| 5,234,431 | 8/1993 | Keller ....................................... | 606/69 |
| 5,258,034 | 11/1993 | Furlong et al. ........................... | 623/23 |
| 5,269,784 | 12/1993 | Mast ......................................... | 606/69 |
| 5,290,288 | 3/1994 | Vignaud et al. .......................... | 606/69 |
| 5,290,313 | 3/1994 | Oudard ..................................... | 623/20 |
| 5,336,225 | 8/1994 | Zang ........................................ | 606/73 |
| 5,387,240 | 2/1995 | Pottengaer et al. ...................... | 623/20 |
| 5,556,433 | 9/1996 | Gabriel et al. ........................... | 623/20 |

FOREIGN PATENT DOCUMENTS

| | | | |
|---|---|---|---|
| 529408A1 | 8/1992 | European Pat. Off. . | |
| 531263A1 | 8/1992 | European Pat. Off. . | |
| 0529408 | 3/1993 | European Pat. Off. ............... | 623/20 |
| 0531263 | 3/1993 | European Pat. Off. . | |
| 0473375 | 3/1929 | Germany .............................. | 411/398 |

OTHER PUBLICATIONS

Paper entitled: "Design Rationale and Testing of a Ported, Proximally Cemented Hip Stem" by M.T. Manley, M.A. Kester, P.O. Merritt, B. Hack, N. dong, Osteonics Corp., Allendale, New Jersey, presented at the 39th Annual Meeting, Orthopedic Research Society, Feb. 15–18, 1993, San Fransico, California.

*Primary Examiner*—David Isabella
*Attorney, Agent, or Firm*—Nutter, McClennen & Fish, LLP

[57] ABSTRACT

A modular prosthesis includes a component having a superior surface and an inferior surface. An elongate aperture having a major axis and a minor axis is defined in the component and a bolt shank is insertable through the elongate aperture in the component to extend beyond the inferior surface thereof. Means are provided for selectably positioning the bolt at one of a number of selected points along the major axis of the elongate aperture. In an illustrated embodiment, the means for positioning the bolt includes more than one seat for a bolt head about the aperture. In another embodiment, the prosthesis includes an adapter having a first end defining a cavity for receiving the shank of the bolt extending from the inferior surface. The adapter includes teeth on the first end that are engagable with at least one or more teeth near the aperture in the component on its inferior surface to fix the cavity, and thus the bolt, at a selected point along the major axis of the aperture. Exemplary prostheses include femoral and tibial components.

24 Claims, 3 Drawing Sheets

've 879,391

MODULAR PROSTHESIS

FIELD OF THE INVENTION

This invention relates to joint prostheses, and more particularly, to modular knee joint prostheses.

BACKGROUND OF THE INVENTION

Knee arthroplasty is a well-known surgical procedure wherein a diseased and/or damaged natural knee joint is replaced by a prosthetic knee joint. A typical knee prosthesis may include a tibial component, a femoral component, and a patellar component. The femoral component generally includes a femoral stem and a pair of spaced-apart condylar portions, the superior surfaces of which articulate with a portion of the tibial component. The femoral stem seats within the medullary canal of a resected femur. Similarly, the tibial component includes a stem implantable into a resected tibia, the stem being secured to a tibial plateau that faces the condylar portions of the femoral component.

As normal anatomical variations preclude the use of a standard size or type of any of the above components, modular prosthetic knees have been developed that allow for limited adaptation or exchange of one or more components to provide a customized prosthesis. With respect to the femoral component, for example, it is known to provide a selection of variously angled and sized femoral stems that are attachable to the remainder of the femoral component with a screw. In practice, the femoral stem is rotated with respect to the femoral component and screw until the femoral stem is tightly bound against a surface of the femoral component and cannot be further rotated. Such a configuration is generally acceptable for a cylindrical, nonangled femoral stem because the radial position at which the femoral stem binds has no effect on the orientation of the femoral stem.

By contrast with a cylindrical femoral stem, a femoral stem having a flattened portion that must be inserted into the medullary canal at a particular orientation or a femoral stem that must be laterally angled with respect to the remainder of the femoral component, the radial stopping point or positioning of the femoral stem is critical. However, it is quite difficult to screw the femoral stem in place and ensure that the femoral stem binds against the femoral component at a predetermined radial point. Additionally, a wide selection of relatively expensive femoral stems must be stocked.

In addition to lateral offset, the size, shape, or condition of a patient's femur sometimes requires that the femoral stem be offset from a central location in either an anterior or posterior direction. Flexible or easily adjusted anterior-posterior offset is not provided by known prostheses. Similar considerations and problems apply to the tibial component.

SUMMARY OF THE INVENTION

The present invention improves upon known devices by providing a modular prosthesis that is readily customized to a patient's anatomical requirements and which provides a bone stem that is readily adjustable with respect to a tibial or femoral component. In an exemplary embodiment of the invention, a modular prosthesis includes a component having a superior surface and an inferior surface. An elongate aperture having a major axis and a minor axis is defined in the component and a bolt shank is insertable through the aperture in the component to extend beyond the inferior surface thereof. Means are provided for selectably positioning and securing the bolt at one of a number of selected points along the major axis of the elongate aperture.

A modular knee prosthesis, for example, includes a femoral component having a superior surface, an inferior surface, a posterior face, and an anterior face. Multiple bolt head seats are formed in the superior surface of the femoral component and they define and/or surround a single elongated aperture. A bolt including a head having a spherical face from which a shank extends is positionable in a selected one of the bolt head seats. The bolt is rotatable with respect to the femoral component and the bolt shank is pivotable toward a first end and a second end of the elongate aperture when the bolt head is positioned in the selected bolt seat. An adapter includes a first end that defines a first cavity for receiving and engaging the shank of the bolt, a second end opposite the first end, and a shank extending from the second end. The first end of the adapter, which is ultimately pressed against the inferior surface of the femoral component when the prosthesis is assembled, defines a plane having an angulation in the range of 0 to 15 degrees or more with respect to a longitudinal axis of the adapter. A femoral stem having a first end that defines a threaded cavity is engagable with the shank extending from the second end of the adapter.

In yet another embodiment, the means for positioning the bolt includes an adapter having teeth on the first end that are engagable with at least one or more teeth near the aperture in the component on its inferior surface to fix the cavity, and thus the bolt, at a selected point along the major axis of the aperture.

BRIEF DESCRIPTION OF THE DRAWINGS

A more complete understanding of the present invention and the attendant advantages and features thereof will be more readily understood by reference to the following detailed description when it is considered in conjunction with the accompanying drawings wherein.

DETAILED DESCRIPTION OF THE INVENTION

Figure 1:
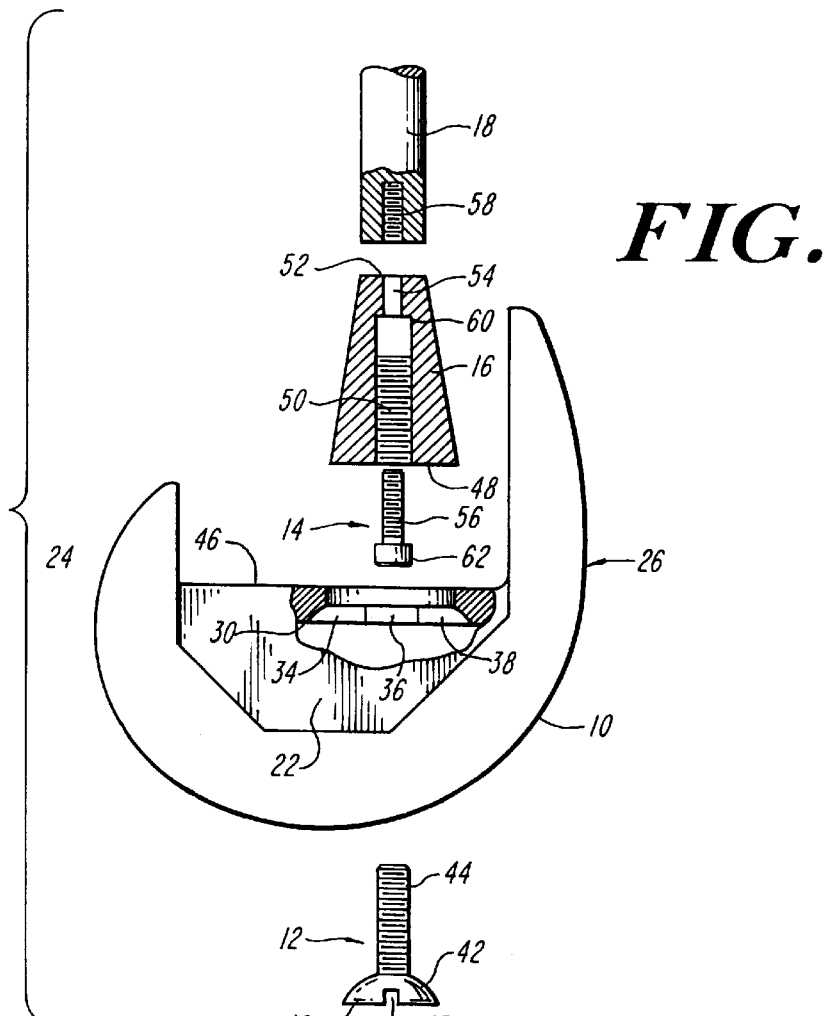
FIG. 1 is a cut-away, exploded view of a modular knee prosthesis according to the present invention.

FIG. 1 illustrates a modular prosthesis, and more particularly a modular knee prosthesis including a femoral component 10, a first bolt 12, a second bolt 14, an adapter 16, and a femoral stem 18. Although the illustrated modular knee prosthesis includes a femoral component 10 adapted for a right knee, the first bolt 12, second bolt 14, adapter 16, and femoral stem 18 are suitable for use, without modification, in association with a femoral component (not shown) adapted for a left knee.

Figure 2:
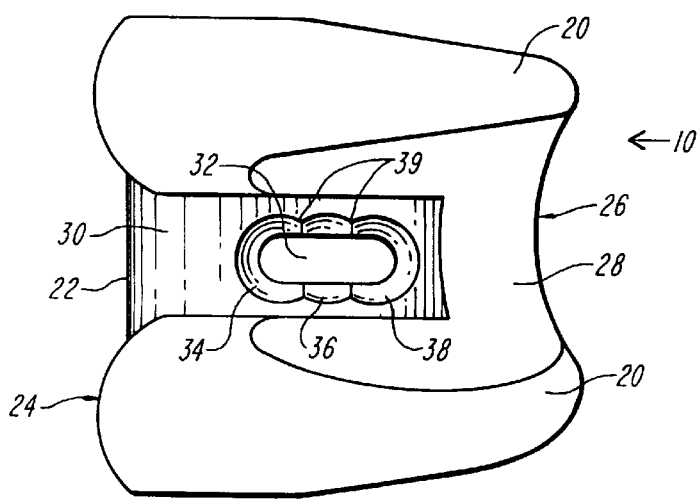
FIG. 2 is plan view of one face of the femoral component of FIG. 1.

Referring to FIG. 2, a view of the femoral component 10 of FIG. 1 is illustrated to show a superior surface including condylar portions 20 that are connected by an inter-condylar region or boss 22. The femoral component 10 has a posterior face 24 and an anterior face 26. The anterior face 26 of the femoral component includes a patellar groove 28.

The boss 22 defines a box-like cavity that extends into the page. One surface 30 of the boss 22 defines an aperture 32 that is elongated in the anterior-posterior direction. For the purposes of the present description, the surface 30 of the boss 22 is considered to be part of the superior surface of the femoral component. The surrounds of the aperture 32 include three spherical receptacles or seats 34, 36, and 38 that define first, second, and third, or posterior, neutral, and anterior bolt positions. The seats can also be referred to as "means for positioning and/or engaging." The spherical or dish-like shape of each seat allows a bolt having a bolt head with a curved head face to be easily rotated with respect to the femoral component or angled in the posterior and anterior directions.

In the illustrated embodiment, the anterior-posterior dimension of the elongate aperture 32 and the diameter of the seats 34, 36, 38 require that the seats overlap or intersect. However, the curvature of the seats at the points of intersection 39 is sufficiently pronounced to distinguish adjoining seats and to prevent a fully seated bolt head from sliding from one seat to an adjacent seat. The less seats overlap, the more secure the seating. Depending on the anterior-posterior dimension of the aperture 32 and the diameter of the seats, the seats may not even overlap.

The anterior-posterior dimension of the aperture 32 is determined by the shank diameter of the first bolt 12, the maximum degree of angulation required for the first bolt, and the spacing between bolt positions as determined by seat location. The lateral dimension of the aperture 32 is determined by the diameter of the shank of the first bolt 12 and is generally just slightly wider than the shank diameter. Although the illustrated embodiment includes a femoral component having an aperture with three seats, other embodiments of the femoral component may have two seats or more than three seats.

Referring again to FIG. 1, the bolt 12 is shown having a bolt head 40 with a curved head face 42 and a threaded shank 44. The head face 42 has a curvature corresponding to the curvature of each of the three seats 34, 36, and 38 and the shank has a length sufficient to extend through the aperture 32 beyond the outer or inferior face 46 of the boss 22. The bolt head 40 includes an engagement means such as a hex socket 45 to enable the first bolt 12 to be rotated with a tool or by hand.

The adapter 16 includes a first end or base 48 that defines an opening leading to a first cavity 50 that is threaded and dimensioned so as to be able to receive and engage the bolt shank 44. The adapter 16 includes a second end 52 that defines an opening and a second cavity 54 that is dimensioned to receive a shank 56 of the second bolt 14. When assembled, a portion of the second bolt 14 is retained within the adapter 16 and a portion of the shank 56 extends from the second cavity beyond the second end 52 of the adapter 16. At least a portion of the shank 56 is threaded and dimensioned so as to be matable with a threaded cavity 58 in the femoral stem 18.

In the illustrated embodiment, the adapter 16 includes a constriction or shoulder 60 that prevents the head 62 of the bolt 14 from entering into the second cavity 54. However, in other non-illustrated embodiments, the second bolt 14, possibly comprising merely a threaded shank portion, is secured to the second end 52 of the adapter by means known to those skilled in the art. For example, a portion of the adapter 16 can be threaded to engage the shank 56.

Embodiments of the adapter 16 are provided that include a first end or base 48 that defines a plane that is perpendicular to the longitudinal axis of the first cavity 50. In other embodiments, the plane defined by the base 48 is angled with respect to the longitudinal axis of the cavity 50. Thus, when the adapter 16 is seated on the inferior face 46 of the boss 22, the longitudinal axes of the first and second cavities are either perpendicular or angled with respect to the inferior face. In exemplary embodiments, the adapter angulation ranges from about 0° to about 15° or more. Accordingly, when the femoral stem 18 is secured to the adapter 16, the femoral stem is provided with substantially the same angular orientation as the adapter. With respect to the adapter of FIG. 1, the base 48 is perpendicular to the longitudinal axis of the first cavity 50 to provide 0° angulation of the adapter.

Figure 3:
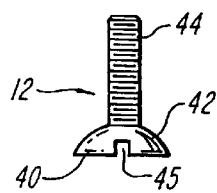
FIG. 3 is a sectional view of an alternative embodiment of the femoral stem and adapter shown in FIG. 1.
Figure 3:
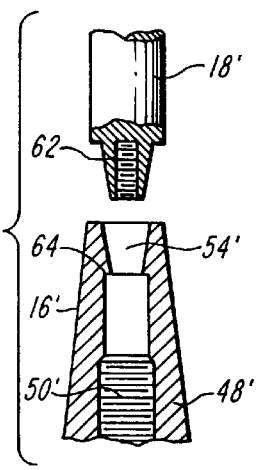

FIG. 3 illustrates an alternative embodiment of an adapter 16' and a femoral stem 18' wherein the adapter includes a first cavity 50' for receiving the bolt shank 44 and a second cavity 54' having a Morse taper for receiving a tapered portion 62 of the femoral stem 18'. Like the femoral stem 18, the femoral stem 18' includes a threaded cavity 63 that is engagable with the shank 56 of the second bolt 14. The second bolt 14 is retained within the adapter 16' in a manner similar to that described with respect to the adapter of FIG. 1. Namely, a constriction or shoulder 64 blocks movement of the head 62 of the second bolt 14 from moving toward or into the second cavity 54'. With respect to the adapter of FIG. 3, a base 48' is canted with respect to the longitudinal axis of the first cavity 50' to provide angulation of the adapter 16'.

An exemplary modular knee prosthesis can be assembled on the following manner. A femoral stem 18, 18' having a desired size and configuration is selected for mating with an adapter 16, 16' having a desired angulation. The second bolt 14 is inserted shank first into the first cavity 50, 50' of the adapter 16, 16' until the bolt head 62 abuts the shoulder 60, 64 and the shank 56 protrudes from the adapter. The selected femoral stem 18, 18' is engaged with the shank 56 and the second bolt 14 is rotated with respect to the femoral stem to draw the femoral stem into a tight abutting relationship with the adapter 16, 16'. The adapter 16, 16' is placed proximate the femoral component 10 and the first bolt 12 is inserted through the aperture 32 in the femoral component and engaged with the adapter. As the first bolt 12 is tightened by rotating it, the bolt head 40 is aligned with one of the first, second or third seats 34, 36, 38 in accordance with the anterior-posterior offset desired. Because the bolt head includes a spherical face 42, the bolt 12 can pivot in the anterior-posterior or medial-lateral direction to match the angulation of the adapter 16, 16'. Before the first bolt 12 is completely tightened, the adapter 16 is positioned by a surgeon at a precise radial orientation with respect to the femoral component 10. The first bolt 12 is then fully tightened so that the bolt head 40 cannot be dislodged from the selected seat and the adapter cannot be rotated with respect to the femoral component 10.

Figure 4:
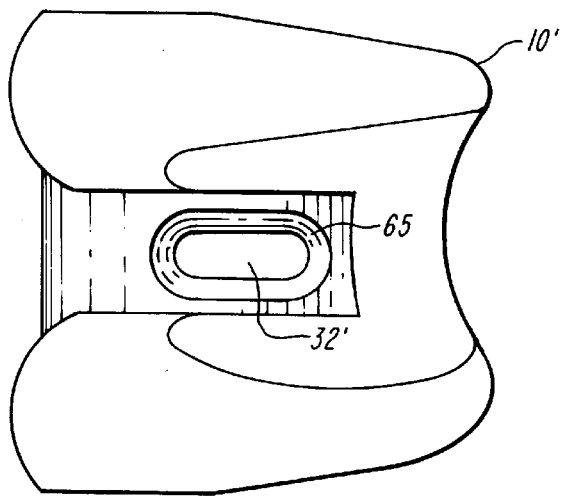
FIG. 4 is a plan view of one face of an alternative embodiment of a femoral component in accordance with the invention.

FIG. 4 is a plan view of one face of an alternative embodiment of a femoral component 10', wherein an elongate aperture 32' through a surface 30' is surrounded by a single, elongate, concentric seat 65. The seat 65 is dimensioned to compliment a bolt having a spherical head face as illustrated with respect to FIG. 1. However, unlike the embodiments illustrated in FIGS. 1–3, placement of the bolt is not limited to one of a number of predetermined locations defined by dish-like seats. Rather, in this embodiment, the bolt is freely movable along the longitudinal axis of the aperture 32' until mated with an adapter as described below.

Figure 5:
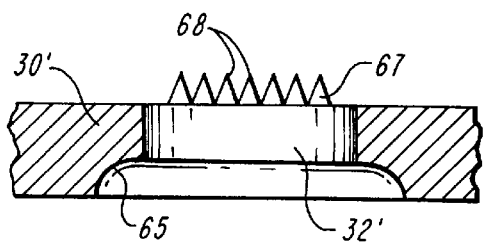
FIG. 5 is a side sectional view of a portion of the femoral component of FIG. 4 that shows serrated teeth proximate the aperture through the component.

FIG. 5 is a side sectional view of a portion of the femoral component of FIG. 4 that shows numerous surface relief elements such as notches, serrations, or teeth 67 on the opposite face of the surface 30' from the concentric seat 65. The teeth 67 are configured to interdigitate or otherwise engage with complimentary teeth, serrations, notches, or other regular or irregular surface relief features on the base of an adapter to permit the adapter to be precisely located and retained at a selected one of numerous possible positions on the femoral component 10' from one end of the aperture 32' to the opposite end thereof. The number of possible engagement positions for the adapter is determined by the length of the aperture 32' and the size, shape, and spacing of the teeth 67. In an exemplary embodiment, crests 68 of the teeth 67 are separated by about 1 mm, thus permitting selection of adapter engagement positions in 1 mm increments.

Figure 6:
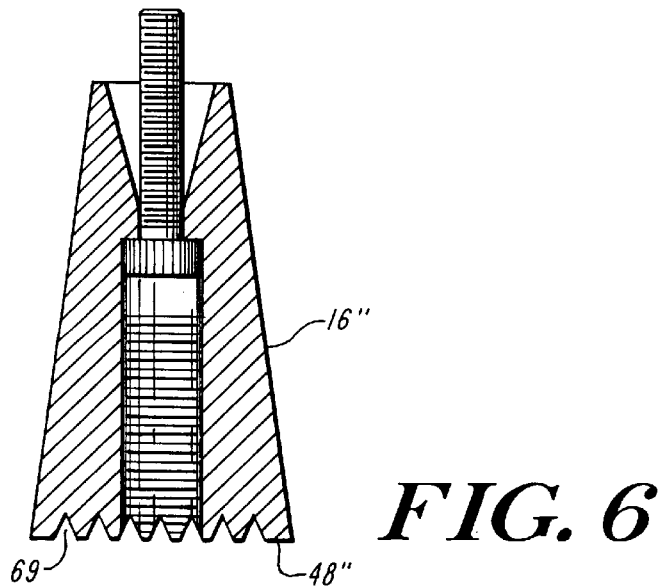
FIG. 6 is a sectional view of an adapter that has a serrated base.

FIG. 6 is a sectional view of an embodiment of the adapter 16" that has a textured, serrated, or notched base 48". As described above, teeth or notches 69 in the base 48" are configured and spaced to engage one or more teeth 67 near or surrounding the aperture 32' of the femoral component 10'. Thus, when the adapter 16" is pressed firmly against the femoral component 10', the adapter is locked into the selected engagement position and will not slide. Additionally, the base 48" of the adapter 16" can be angled as shown in FIG. 3 to establish a selected valgus angulation for a femoral stem. The remaining components and features of the modular prosthesis are substantially identical with the components and features described with respect to the preceding embodiments.

Although the invention has been described with respect to a modular femoral prosthesis, it should be understood that embodiments of the elongated slot with multiple seats or teeth have applicability to any orthopedic implant that could benefit from a selectably positionable bolt, adapter, or bone stem. For example, a tibial component for a knee prosthesis can benefit from the ability to selectably position a stem and/or an adapter with respect to a plateau or base portion.

Figure 7:
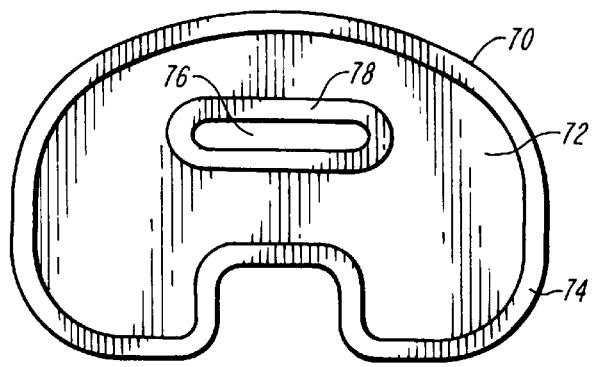
FIG. 7 is a plan view of one face of a tibial plateau base plate.
Figure 10:
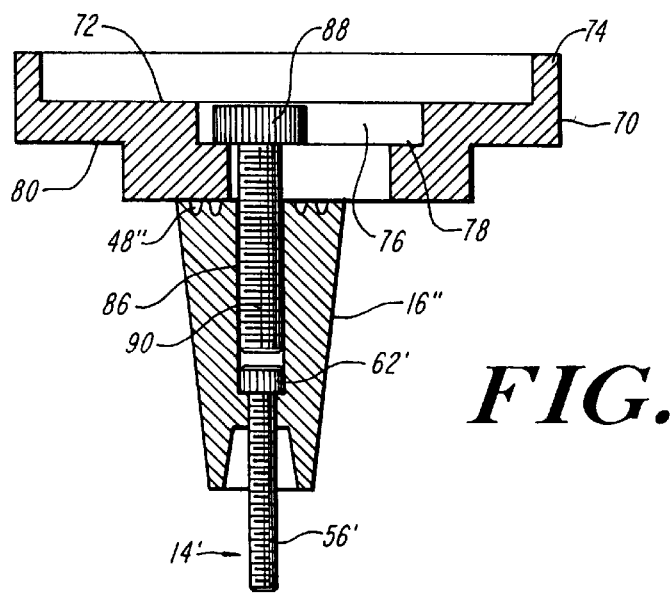
FIG. 10 is a side sectional view of the tibial plateau base plate of FIG. 7 mated with an adapter having a serrated base.

FIG. 7 is a plan view of a tibial plateau base plate 70 having a first face, hereinafter referred to as the superior surface 72. In the illustrated embodiment, a portion of the superior surface 72 of the base plate includes a peripheral ridge or elevation 74. The base plate defines an elongated slot or aperture 76 surrounded by a counter bore 78. The short axis length of the aperture 76 is determined by the diameter of a bolt shank to be inserted through the aperture. The short axis diameter of the counter bore 78 is determined by the diameter of a bolt head, so that when a bolt shank is inserted through the aperture 76 from the superior surface side of the base plate, the head of the bolt shank engages the counter bore. Additionally, the counter bore 78 can be sunk into the base plate 70 a distance to cause the head of the bolt to be flush with, above, or below a portion of the superior surface 72. FIG. 10, for example, illustrates the head of a bolt that is flush with the superior surface 72. The long axis length of the aperture 76, shown here oriented laterally with respect to the base plate 70, is determined by the desired range of lateral offset positions desired.

Figure 8:
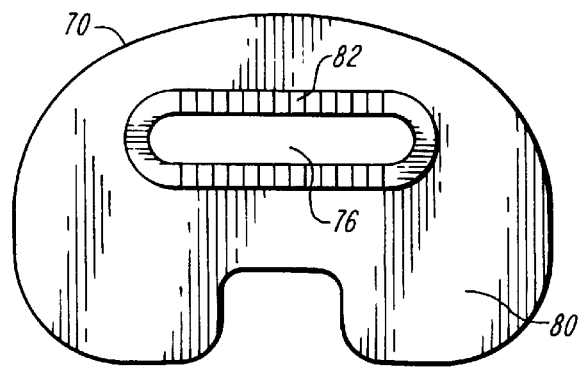
FIG. 8 is a plan view of a second face of the tibial plateau base plate of FIG. 7.

FIG. 8 illustrates a second face, hereinafter referred to as the inferior surface 80, wherein the elongate aperture 76 is surrounded with numerous notches or teeth 82. The teeth 82 are configured to interdigitate and engage with complimentary teeth or notches on the base of an adapter, as shown in FIGS. 6 and 10, to allow the adapter to be retained at a selected one of numerous possible positions on the base plate 70 from one end of the aperture 76 to the opposite end thereof.

Figure 9:
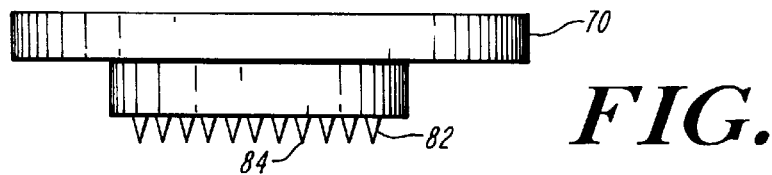
FIG. 9 is a side view of the tibial plateau base plate of FIG. 7.

FIG. 9 is a side view of a portion of the base plate 70 that shows the teeth 82 in greater detail. The number of possible engagement positions for the adapter is determined by the length of the aperture 70 and the size, shape, and spacing of the teeth 82. In an exemplary embodiment, crests 84 of the teeth 82 are separated by about 1 mm, thus permitting selection of lateral adapter engagement positions in 1 mm increments.

FIG. 10 is a side sectional view of the tibial plateau base plate of FIG. 7 mated with an adapter 16" having a serrated base 48". A bolt 86 having a cylindrical head 88 and a threaded shank 90 is shown in threaded engagement with the adapter 16" having its base 48' tightly interfitted with the teeth 82 of the base plate 70. A second bolt 14' having a head 62' and a shank 56' is retained within the adapter 16" for engagement with a tibial stem (not shown).

The illustrated embodiments have included an adapter interposed between the femoral stem and the femoral component or the tibial stem and the tibial plateau. However, other embodiments of the invention are contemplated wherein a femoral or tibial stem is provided having a flat or canted base and wherein the femoral or tibial stem is adapted for direct mating with the first bolt so that the base of the femoral or tibial stem is bound directly against the femoral component or tibial plateau. Even when an adapter is provided, the first bolt can extend completely through the adapter and directly engage the femoral or tibial stem. In yet other embodiments of the prosthesis, the base of the femoral or tibial stem can be notched or provided with teeth as described above with respect to the base of the adapter.

Although the invention has been shown and described with respect to exemplary embodiments thereof, various other changes, omissions and additions in form and detail thereof may be made therein without departing from the spirit and scope of the invention.

What is claimed is:

1. A modular prosthesis comprising:
   a component of an articulating knee joint having a superior surface and an inferior surface defining a elongate aperture having a major axis and a minor axis;
   a bolt having a shank and a head, the bolt shank being insertable through the elongate aperture in the component to extend beyond the inferior surface, and the bolt head being engagable with the component to inhibit movement of the bolt through the component; and
   means for selectably positioning the bolt at selected points along the major axis of the elongate aperture.

2. The modular prosthesis of claim 1, wherein the component further includes a posterior face; and the means for selectably positioning the bolt includes a plurality of bolt head seats formed in the superior surface of the component.

3. The modular prosthesis of claim 2, wherein each of the bolt head seats is defined by a spherical depression in the superior surface of the femoral component.

4. The modular prosthesis of claim 3, wherein adjacent head seats overlap.

5. The modular prosthesis of claim 4, wherein the elongated aperture has a major axis oriented in an anterior-posterior direction, a center point, a first aperture end along the major axis between the anterior face and the center point, a second aperture end along the major axis between the posterior face and the center point, and wherein the plurality of bolt head seats consists of a first bolt head seat proximate the first aperture end, a second bolt head seat proximate the center point, and a third bolt head seat proximate the second aperture end.

6. The modular prosthesis of claim 2, further comprising a bolt including a head portion engagable with a selected one of the plurality of bolt head seats to inhibit movement of the bolt through the aperture, and an elongate shaft portion extending from the head portion of the bolt, the elongate shaft portion having a length sufficient to protrude through the aperture in the component and beyond the inferior surface of the component.

7. The modular prosthesis of claim 3, further comprising a bolt including a head having a spherical face from which a shank extends, the spherical face positionable in a selected one of the plurality of bolt head seats, wherein the bolt is rotatable with respect to the component and the bolt shank is alternately pivotable toward a first end and a second end of the elongate aperture when the bolt head is positioned in the selected bolt seat.

8. The modular prosthesis of claim 7, wherein the shank is threaded.

9. The modular prosthesis of claim 7, further comprising an adapter having a first end defining a first cavity for receiving and engaging the shank of the bolt.

10. A modular prosthesis comprising:
a femoral component having a superior surface and an inferior surface that define an elongate aperture having a major axis and a minor axis, a posterior face, and an anterior face;
a bolt having a shank and a head, the bolt shank being insertable through the elongate aperture in the component to extend beyond the inferior surface, and the bolt head being engagable with the component to inhibit movement of the bolt through the component;
means for selectably positioning the bolt at selected points along the major axis of the elongate aperture, the means for selectably positioning the bolt including a plurality of bolt head seats formed in the superior surface of the femoral component, the plurality of bolt head seats defining a single elongated aperture, wherein each of the bolt head seats is defined by a spherical depression in the superior surface of the femoral component;
a bolt including a head having a spherical face from which a shank extends, the spherical face positionable in a selected one of the plurality of bolt head seats, wherein the bolt is rotatable with respect to the femoral component and the bolt shank is alternately pivotable toward a first end and a second end of the elongate aperture when the bolt head is positioned in the selected bolt seat; and
an adapter having a first end defining a first cavity for receiving and engaging the shank of the bolt, wherein the adapter includes a second end opposite the first end, and a threaded shank extending from the second end.

11. A modular prosthesis comprising:
a femoral component having a superior surface and an inferior surface that define an elongate aperture having a major axis and a minor axis, a posterior face, and an anterior face;
a bolt having a shank and a head, the bolt shank being insertable through the elongate aperture in the component to extend beyond the inferior surface, and the bolt head being engagable with the component to inhibit movement of the bolt through the component;
means for selectably positioning the bolt at selected points along the major axis of the elongate aperture, the means for selectably positioning the bolt including a plurality of bolt head seats formed in the superior surface of the femoral component, the plurality of bolt head seats defining a single elongated aperture, wherein each of the bolt head seats is defined by a spherical depression in the superior surface of the femoral component;
a bolt including a head having a spherical face from which a shank extends, the spherical face positionable in a selected one of the plurality of bolt head seats, wherein the bolt is rotatable with respect to the femoral component and the bolt shank is alternately pivotable toward a first end and a second end of the elongate aperture when the bolt head is positioned in the selected bolt seat;
an adapter having a first end defining a first cavity for receiving and engaging the shank of the bolt; and
a second bolt having a bolt head engagable with a constriction in the adapter that is narrower than the bolt head, and a shank extending from the bolt head to a point external to the adapter.

12. The modular prosthesis of claim 10, further including a femoral stem having a first end that defines a threaded cavity that is engagable with the threaded shank.

13. A modular prosthesis comprising:
a femoral component having a superior surface and an inferior surface that define an elongate aperture having a major axis and a minor axis, a posterior face, and an anterior face;
a bolt having a shank and a head, the bolt shank being insertable through the elongate aperture in the component to extend beyond the inferior surface, and the bolt head being engagable with the component to inhibit movement of the bolt through the component;
means for selectably positioning the bolt at selected points along the major axis of the elongate aperture, the means for selectably positioning the bolt including a plurality of bolt head seats formed in the superior surface of the femoral component, the plurality of bolt head seats defining a single elongated aperture, wherein each of the bolt head seats is defined by a spherical depression in the superior surface of the femoral component;
a bolt including a head having a spherical face from which a shank extends, the spherical face positionable in a selected one of the plurality of bolt head seats, wherein the bolt is rotatable with respect to the femoral component and the bolt shank is alternately pivotable toward a first end and a second end of the elongate aperture when the bolt head is positioned in the selected bolt seat; and
an adapter having a first end defining a first cavity for receiving and engaging the shank of the bolt, wherein the adapter includes a second end that defines a cavity having a Morse taper.

14. The modular prosthesis of claim 9, wherein the first cavity of the adapter has a longitudinal axis and the first end of the adapter defines a plane that is perpendicular to the longitudinal axis.

15. The modular prosthesis of claim 9, wherein the first cavity of the adapter has a longitudinal axis and the first end of the adapter defines a plane that is angled with respect to the longitudinal axis.

16. The modular prosthesis of claim 9, wherein the first cavity of the adapter has a longitudinal axis and the first end of the adapter defines a plane having an angulation in the range of 0 to 15 degrees with respect to the longitudinal axis.

17. A modular prosthesis comprising:

a prosthetic component of an articulating knee joint having a superior surface and an inferior surface;

a plurality of overlapping, spherical bolt head seats formed in the superior surface of the prosthetic component, the plurality of bolt head seats defining a single elongated aperture, wherein the elongated aperture has a major axis, a center point, a first aperture end along the major axis, a second aperture end along the major axis opposite the first aperture end, and wherein the plurality of bolt head seats consists of a first bolt head seat proximate the first aperture end, a second bolt head seat proximate the center point, and a third bolt head seat proximate the second aperture end; and a bolt including a head having a spherical face from which a shank extends, the spherical face positionable in a selected one of the plurality of overlapping, spherical bolt head seats, wherein the bolt is rotatable with respect to the prosthetic component and the bolt shank is pivotable toward a first end and a second end of the elongate aperture when the bolt head is positioned in the selected bolt seat.

18. The modular prosthesis of claim 17, further comprising an adapter having a first end defining a first cavity for receiving and engaging the shank of the bolt, a second end opposite the first end, and a threaded shank extending from the second end.

19. The modular prosthesis of claim 18, further including a stem having a first end that defines a threaded cavity that is engagable with the threaded shank.

20. The modular prosthesis of claim 19, wherein the first cavity of the adapter has a longitudinal axis and the first end of the adapter defines a plane having an angulation in the range of 0 to 15 degrees with respect to the longitudinal axis.

21. The modular prosthesis of claim 1, wherein the means for selectably positioning the bolt includes a plurality of teeth proximate the aperture on the inferior side of the component; and an adapter having a first end defining a first cavity for receiving the shank of the bolt, the first end of the adapter being engagable with at least one of the teeth to fix the first cavity of the adapter at a selected point along the major axis of the single elongate aperture of the component.

22. The modular prosthesis of claim 21, wherein the adapter includes a plurality of teeth on the first end of the adapter.

23. The modular prosthesis of claim 22, wherein the teeth are separated from each other by about one millimeter.

24. A modular prosthesis comprising:

a component having a superior surface and an inferior surface defining a single elongate aperture having a major axis and a minor axis;

a bolt having a shank and a head, the bolt shank being insertable through the single elongate aperture in the component to extend beyond the inferior surface, and the bolt head being engagable with the component to inhibit movement of the bolt with respect to the component;

means for selectably positioning the bolt at selected points along the major axis of the single elongate aperture of the component, wherein the means for selectably positioning the bolt includes a plurality of teeth around the aperture on the inferior side of the component;

an adapter having a first end and a second end, the first end defining a first cavity for receiving the shank of the bolt, the first end of the adapter including a plurality of teeth engagable with at least one of the teeth around the aperture to fix the first cavity of the adapter at a selected point along the major axis of the single elongate aperture of the component; and a stem adapted for insertion into a bone, the stem being securable to the second end of the adapter.

* * * * *